US006680316B1

(12) United States Patent
Ohkuchi et al.

(10) Patent No.: US 6,680,316 B1
(45) Date of Patent: Jan. 20, 2004

(54) PYRIDAZIN-3-ONE DERIVATIVES AND MEDICINES CONTAINING THE SAME

(75) Inventors: Masao Ohkuchi, Tokorozawa (JP); Yoshinori Kyotani, Higashiyamato (JP); Hiromichi Shigyo, Fuchu (JP); Hideo Yoshizaki, Sayama (JP); Tomoyuki Koshi, Shiki (JP); Takahiro Kitamura, Higashimurayama (JP); Takayuki Matsuda, Higashimurayama (JP); Kyoko Yasuoka, Higashiyamato (JP); Tomoko Furuyama, Tokyo (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/926,040

(22) PCT Filed: Feb. 25, 2000

(86) PCT No.: PCT/JP00/01098

§ 371 (c)(1),
(2), (4) Date: Aug. 20, 2001

(87) PCT Pub. No.: WO00/50408

PCT Pub. Date: Aug. 31, 2000

(30) Foreign Application Priority Data

Feb. 26, 1999 (JP) .............................................. 11-49758

(51) Int. Cl.[7] .................... C07D 237/24; C07D 403/06; C07D 401/12; A61K 31/50

(52) U.S. Cl. ............. 514/247; 514/252.03; 514/252.06; 544/238; 544/239

(58) Field of Search ................................ 544/238, 239; 514/247, 252.03, 252.06

(56) References Cited

U.S. PATENT DOCUMENTS

| | | | |
|---|---|---|---|
| 3,840,597 A | 10/1974 | Moore et al. | 260/556 F |
| 4,238,490 A | 12/1980 | Powers et al. | 424/250 |
| 4,545,810 A | 10/1985 | Pyne et al. | 71/92 |
| 4,954,518 A | 9/1990 | Takano et al. | 514/456 |
| 6,348,468 B1 | 2/2002 | Ohkuchi et al. | 514/247 |
| 6,403,586 B1 | 6/2002 | Ohkuchi et al. | 514/252.03 |

FOREIGN PATENT DOCUMENTS

| | | | |
|---|---|---|---|
| DE | 23 33 643 | | 1/1974 |
| EP | 18 063 | | 10/1980 |
| EP | 46 069 | | 2/1982 |
| EP | 0 376 288 | | 7/1990 |
| EP | 0 628 550 | | 12/1994 |
| GB | 788393 | * | 1/1958 |
| JP | 7-69894 | | 3/1995 |
| JP | 7-503017 | | 3/1995 |
| WO | WO 93/14081 | | 7/1993 |
| WO | WO 97/05878 | | 2/1997 |
| WO | WO 99/10331 | | 3/1999 |
| WO | WO 99/10332 | | 3/1999 |
| WO | WO 99/25697 | * | 5/1999 |
| WO | WO 00/24719 | | 5/2000 |

OTHER PUBLICATIONS

ATCC Cell Lines and Hybridomas, 8th Edition, 1994.*
Batra et al., Derivatives of 5,6–Diphenylpyridazin–3–one: Synthetic Antimitotic Agents Which Interact with Plant and Mammalian Tubulin at a New Drug–binding Site, Cancer Research, 46(4 pt. 2) pp. 1889–1893, 1986.*
Damasio, Alzheimer's Disease and Related Dementias, Cecil Textbook of Medicine, 20th Edition, vol. 2, pp. 1992–1996, 1996.*
Iijima, PubMed Abstract (Masui, 47(6):662–77), Jun. 1998.*
J.K. Batra, et al., Cancer Research, vol. 46, No. 4 pt. 2, pp. 1889–1893, "Derivatives of 5,6–Diphenylpyridazin–3–One: Synthetic Antimitotic Agents Which Interact with Plant and Mammalian Tubulin at a New Drug–Binding Site", Apr. 1986.
R. Buchman, et al., Journal of Medicinal Chemistry, vol. 23, No. 12, pp. 1398–1405, "Antihypertensive 5,6,–Diarylpyridazin–3–Ones", 1980.
Taisho, 1 page, "KE–298", Jan. 19, 1999.
H. Ohzeki, et al., The Japan Inflamation Academy (11th Session), p. 75, "Antirheumatic Activities of KE–298, Having an Effect on IL–1 (1st Report)", Jul. 20 and 21, 1990 (with English translation).
J. Bondeson, et al., Biochemical Pharmacology, vol. 52, pp. 35–42, "Differencial Effects of Tenidap on the Zymosan— and Lipopolysaccharide–Included Expression of mRNA for Proinflammatory Cytokines in Macrophages", 1996.

(List continued on next page.)

Primary Examiner—Deepak Rao
(74) Attorney, Agent, or Firm—Oblon, Spivak, McClelland, Maier & Neustadt, P.C.

(57) ABSTRACT

Objects of the invention are to provide compounds having excellent activity against interleukin-1β production and also medicines comprising them as effective ingredients.

Pyridazin-3-one derivatives represented by the following formula (1):

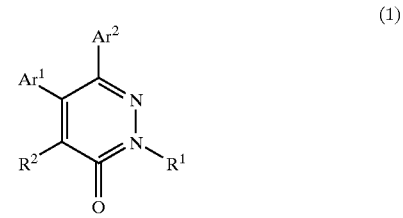

(1)

wherein $Ar^1$ represents a substituted or unsubstituted aromatic group, $Ar^2$ represents a phenyl group having a substituent at least at the 4-position thereof, $R^1$ represents a linear or branched alkyl group, an alkyl group having a cyclic structure, a substituted or unsubstituted phenyl group or a substituted or unsubstituted phenyl(lower alkyl) group, and $R^2$ represents a cyano group, a carboxyl group, a (lower alkoxy)carbonyl group, a substituted or unsubstituted lower alkyl group or a substituted or unsubstituted carbamoyl group, or salts thereof; and medicines comprising them as effective ingredients.

18 Claims, No Drawings

OTHER PUBLICATIONS

V. Casini–Raggi, et al., Gastroenterology, vol. 109, No. 3, pp. 812–818, "Anti–Inflammatory Effects of CGP 47969A, A Novel Inhibitor of Proinflammatory Cytokine Synthesis, In Rabbit Immune Colitis", 1995.

G. Ku, et al., Cytokine, vol. 8, No. 5, pp. 377–386, "Interleukin–1β Converting Enzyme Inhibition Blocks Progression of Type II Collagen–Included Arthritis in Mice", May 1996.

G. Nannini, et al., Eur. J. Med. Chem.—Chimica Therapeutica, vol. 14, No. 1, pp. 53–60, "Synthesis and Pharmacological Activity of Some 5,6–Diphenyl–Pyridazines", 1979.

M. Tanaka, et al., Eur. J. Med. Chem. vol. 31, pp. 187–198, "Hydroxindole Derivatives as Inhibitors of IL–1 Generation. II. Synthesis and Pharmacological Activities of (E)–3–(7–Hydroxy–6–Methoxyindole–4–yl)–2–Methylpropenoic Acid Derivatives", 1996.

* cited by examiner

PYRIDAZIN-3-ONE DERIVATIVES AND MEDICINES CONTAINING THE SAME

TECHNICAL FIELD

This invention relates to novel pyridazin-3-one derivatives, which have excellent inhibitory activity against interleukin-1β production and are useful for the prevention and treatment of immune system diseases, inflammatory diseases, ischemic diseases and the like, and also to medicines containing them as effective ingredients.

BACKGROUND ART

In many diseases, for example, rheumatism, arthritis, osteoporosis, inflammatory colitis, immune deficiency syndrome, ichorrhemia, hepatitis, nephritis, ischemic diseases, insulin-dependent diabetes mellitus, arterial sclerosis, Parkinson's disease, Alzheimer's disease, leukemia and the like, stimulation of interleukin-1β production, an inflammatory cytokine, is observed. This interleukin-1β serves to induce synthesis of an enzyme which is considered to take part in inflammation like collagenase and PLA2 and, when intra-articularly injected to animals, causes multi-articular destruction highly resembling rheumatoid arthritis. In the normal living body, on the other hand, interleukin-1β is controlled in activity by interleukin-1 receptor, soluble interleukin-1 receptor and interleukin-1 receptor antagonist.

From research conducted making use of recombinants of these bioactivity-inhibiting substances, anti-interleukin-1β antibodies and anti-receptor antibodies against various disease models, interleukin-1β has been found to play an important role in the body, leading to an increasing potential of substances having interleukin-1β inhibitory activity as therapeutics for such diseases.

For example, immunosuppressors and steroids which are used for the treatment of rheumatism out of such many diseases have been reported to inhibit the production of interleukin-1β. Even among medicaments currently under development, KE298, a benzoylpropionic acid derivative [The Japanese Society of Inflammation (11th), 1990], for example, has been reported to,have inhibitory activity against interleukin-1β production although it is an immunoregulator. Inhibitory activity against interleukin-1β production is also observed on a group of compounds which are called "COX-2 selective inhibitors", for example, nimesulide as a phenoxysulfonanilide derivative (DE 2333643), T-614 as a phenoxybenzopyran derivative (U.S. Pat. No. 4,954,518), and tenidap (hydroxyindole derivative) as a dual inhibitor (COX-1/5-LO).

For all of these compounds, however, interleukin-1β production inhibitory activity is not their primary action so that their inhibitory activity against interleukin-1β production is lower than their primary action.

In recent years, increasingly active synthesis research is under way with a focus placed on inhibitory activity against interleukin-1β production. Production inhibitors can be classified into a group of compounds which inhibit the transfer process of an inflammatory signal to a cell nucleus and another group of compounds which inhibit an enzyme ICE that functions in the processing of a precursor of interleukin-1β. Known examples of compounds presumed to have the former action include SB203580 [Japanese Language Laid-Open (Kokai) Publication (PCT) No. HEI 7-503017], FR167653 (Eur. J. Pharm., 327, 169–175, 1997), E-5090 (EP 376288), CGP47969A (Gastroenterology, 109, 812–828, 1995), hydroxyindole derivatives (Eur. J. Med. Chem. 31, 187–198, 1996), and triarylpyrrole derivatives (WO 97/05878), while known examples of compounds presumed to have the latter action include VE-13,045 which is a peptide compound (Cytokine, 8(5), 377–386, 1996).

None of these compounds can however exhibit sufficient inhibitory activity against interleukin-1β production.

On the other hand, it is known that a variety of 5,6-diphenylpyridazine derivatives have analgesic and anti-inflammatory action (Eur. J. Med. Chem., 14, 53–60, 1979). Absolutely nothing has however been known with respect to inhibitory activity of these 5,6-diphenylpyridazine derivatives against interleukin-1β production.

Accordingly, an object of the present invention is to provide a compound having excellent inhibitory activity against interleukin-1β production and also a medicine containing it as an effective ingredient.

DISCLOSURE OF THE INVENTION

Under such circumstances, the present inventors have proceeded with an extensive investigation. As a result, it has been found that pyridazin-3-one derivatives represented by the below-described formula (1) have excellent inhibitory activity against interleukin-1β production and are useful as medicines for the prevention and treatment of immune system diseases, inflammatory diseases and ischemic diseases, leading to the completion of the present invention.

Namely, the present invention provides a pyridazin-3-one derivative represented by the following formula (1):

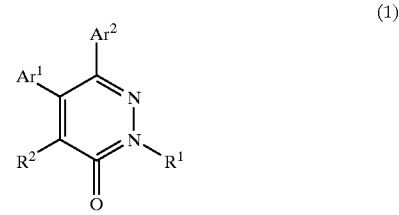

wherein $Ar^1$ represents a substituted or unsubstituted aromatic group, $Ar^2$ represents a phenyl group having a substituent at least at the 4-position thereof, $R^1$ represents a linear or branched alkyl group, an alkyl group having a cyclic structure, a substituted or unsubstituted phenyl group or a substituted or unsubstituted phenyl(lower alkyl) group, and $R^2$ represents a cyano group, a carboxyl group, a (lower alkoxy)carbonyl group, a substituted or unsubstituted lower alkyl group or a substituted or unsubstituted carbamoyl group; or a salt thereof.

The present invention also provides a medicine comprising the pyridazin-3-one derivative (1) or the salt thereof as an effective ingredient.

Further, the present invention also provides an inhibitor of interleukin-1β production comprising the pyridazin-3-one derivative (1) or the salt thereof as an effective ingredient.

Furthermore, the present invention also provides a pharmaceutical composition comprising the pyridazin-3-one derivative (1) or the salt thereof and a pharmaceutically acceptable carrier.

Moreover, the present invention also provides use of the pyridazin-3-one derivative (1) or the salt thereof as a medicine.

In addition, the present invention also provides a method for treating a disease caused by stimulation of interleukin-1β production, which comprises administering the pyridazin-3-one derivative (1) or the salt thereof.

BEST MODE FOR CARRYING OUT THE INVENTION

The pyridazin-3-one derivative according to the present invention is represented by the formula (1).

In the formula (1), examples of the aromatic group represented by $Ar^1$ can include all aromatic hydrocarbon groups and heterocyclic aromatic groups, such as phenyl, naphthyl, pyridyl and quinolyl groups, with a phenyl group being particularly preferred. Illustrative of one or more substituents which the aromatic group may have are halogen atoms, lower alkoxy group,s lower alkylthio groups, lower alkylsulfinyl groups, and lower alkylsulfonyl groups. Examples of the halogen atoms can include fluorine, chlorine, bromine and iodine atoms. Examples of the lower alkyl moieties in the lower alkoxy, lower alkylthio, lower alkylsulfinyl and lower alkylsulfonyl groups can include linear, branched or cyclic alkyl groups having 1 to 6 carbon atoms, for example, methyl, ethyl, n-propyl, isopropyl, n-butyl, isobutyl and t-butyl groups. Among these substituents, lower alkoxy groups are preferred with a methoxy group being particularly preferred.

Illustrative of the substituent which the substituted phenyl group represented by $Ar^2$ has at the 4-position thereof are lower alkoxy, lower alkylthio, lower alkylsulfinyl and lower alkylsulfonyl groups. More specifically, groups similar to those exemplified above in connection with $Ar^1$ can be mentioned, with lower alkoxy groups, especially a methoxy group being preferred. Further, the substituted phenyl group may be substituted at other position or positions by halogen atoms, lower alkoxy groups or the like. Examples of these halogen atoms and lower alkoxy groups can be similar to those exemplified above in connection with $Ar^1$ can be mentioned.

Illustrative of the linear or branched alkyl group represented by $R^1$ are those having 2 to 11 carbon atoms, for examples, ethyl, n-propyl, isopropyl, n-butyl, isobutyl, t-butyl, pentyl, hexyl and heptyl groups. Illustrative of the alkyl groups having cyclic structures are cycloalkyl groups having 3 to 7 carbon atoms, such as cyclopropyl, cyclobutyl, cyclopentyl and cyclohexyl groups; and lower alkyl groups, such as methyl and ethyl groups, with such cycloalkyl groups substituted thereon. Examples of substituent groups on the substituted phenyl or phenyl(lower alkyl) group represented by $R^1$ can include halogen atoms, lower alkyl groups, and lower alkoxy groups. Examples of these halogen atoms, lower alkyl groups and lower alkoxy groups can be similar to those exemplified above in connection with $Ar^1$.

Examples of substituents on the substituted lower alkyl group represented by $R^2$ can include halogen atoms, hydroxy groups, and substituted or unsubstituted phthalimido groups. Illustrative of substituents on the phthalimide groups are halogen atoms, nitro groups, lower alkoxy groups, and amino groups which may contain, as substituents, lower alkyl groups, lower alkylsulfonyl groups or lower alkylcarbonyl groups. Illustrative of the substituent or substituents on the substituted carbamoyl group represented by $R^2$ are lower alkyl groups, aromatic groups, and lower alkyl groups substituted by aromatic groups. Illustrative of the lower alkyl moiety or moieties of the substituted lower alkyl or lower alkoxycarbonyl group represented by $R^2$, the halogen atom or atoms as substituent or substituents of the substituted lower alkyl or lower alkoxy carbonyl group, the lower alkyl moieties of the lower alkyl, lower alkoxy, lower alkylsulfonyl, lower alkylcarbonyl and aromatic-group-substituted lower alkyl group, and the aromatic moieties of the aromatic group and aromatic-group-substituted lower alkyl group can be similar to those exemplified above in connection with $Ar^1$. As the aromatic group, a phenyl or pyridyl group is particularly preferred.

Preferred specific examples of the pyridazin-3-one derivative (1) according to the present invention can include 5,6-bis(4-methoxyphenyl)-4-carbamoyl-2-cyclopropylmethyl-2H-pyridazin-3-one, 5,6-bis(4-methoxyphenyl)-4-cyano-2-ethyl-2H-pyridazin-3-one, 5,6-bis(4-methoxyphenyl)-4-cyano-2-cyclopropylmethyl-2H-pyridazin-3-one, 5,6-bis(4-methoxyphenyl)-4-cyano-2-cyclopentylmethyl-2H-pyridazin-3-one, 2-benzyl-5,6-bis(4-methoxyphenyl)-4-ethoxycarbonyl-2H-pyridazin-3-one, 5,6-bis(4-methoxyphenyl)-4-ethoxycarbonyl-2-isopropyl-2H-pyridazin-3-one, and 5,6-bis(4-methoxyphenyl)-2-isobutyl-4-phthalimidomethyl-2H-pyridazin-3-one.

Illustrative of the salts of the pyridazin-3-one derivative (1), said salt also pertaining to the present invention, are the hydrochloride, nitrate, hydrobromide, acetate, sulfate, p-toluenesulfonate, methanesulfonate, fumarate, succinate, lactate, sodium salt, potassium salt, magnesium salt, calcium salt, ammonium salt, methylammonium salt, dimethylammonium salt, and trimethylammonium. Further, the pyridazin-3-one derivative (1) or the salt thereof according to the present invention may exist in the form of a keto-enol tautomer and solvates. Such tautomer and solvates should also be encompassed by the present invention.

No particular limitation is imposed on a process for the preparation of the pyridazin-3-one (1) or the salt thereof according to the present invention, and a variety of processes, which have conventionally been used for the synthesis of pyridazine derivatives, and their modifications can be used. The pyridazin-3-one derivative (1) according to the present invention can be prepared, for example, by the following reaction scheme.

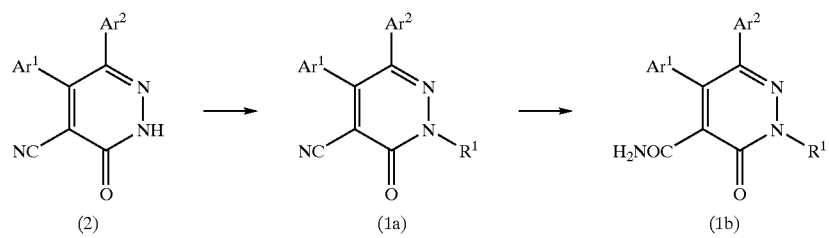

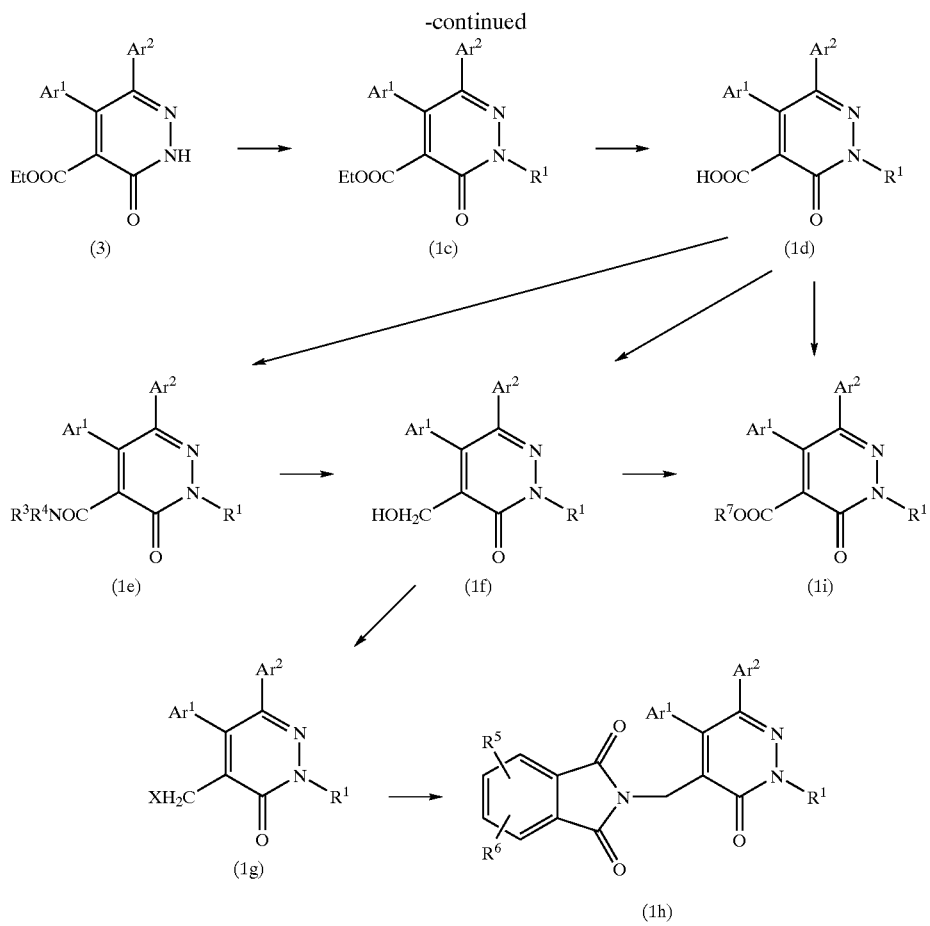

wherein $Ar^1$, $Ar^2$, $R^1$ and $R^2$ have the same meanings, $R^3$ and $R^4$ may be the same or different and each independently represents a hydrogen atom, a lower alkyl group, an aromatic group or an aromatic-group-substituted lower alkyl group, X represents a halogen atom, $R^5$ and $R^6$ may be the same or different and each independently represent a hydrogen atom, a halogen atom, a nitro group, a lower alkoxy group, or an amino group which may have, as substituent or substituents, one or two of lower alkyl groups, lower alkylcarbonyl groups and lower alkylsulfonyl groups, and $R^7$ represents a lower alkyl group.

The starting materials, i.e., the compounds represented by the formula (2) and (3), respectively, can be prepared by known processes (J. Med. Chem., 23, 1398–1405, 1980; Eur. J. Med. Chem., 14, 53–60, 1979).

(A) Preparation of a Compound (1a) in Which $R^2$ is a Cyano Group

This cyano-substituted pyridazin-3-one derivative can be prepared by reacting a compound, which is represented by $R^1$—Y in which $R^1$ has the same meaning as defined above and Y represents a halogen atom or a reactive esterified hydroxyl group, with a compound represented by the formula (2) in the presence of a base in a solvent.

Examples of the base usable in the reaction can include inorganic bases such as potassium carbonate and sodium carbonate and organic bases such as metal alkoxides. Usable examples of the solvent can include N,N-dimethylformamide, dimethylsulfoxide, acetone and methyl ethyl ketone. The reaction may be conducted preferably at 20 to 150° C. for 1 to 20 hours, notably at 50 to 130° C. for 2 to 10 hours.

(B) Preparation of a Compound (1b) in Which $R^2$ is a Carbamoyl Group

This carbamoyl-substituted pyridazin-3-one derivative (1b) can be prepared by reacting a base, such as caustic soda or caustic potash, with the compound (1a) in a solvent.

(C) Preparation of a Compound (1c) in Which $R^2$ is, an Ethoxycarbonyl Group

This ethoxycarbonyl-substituted pyridazin-3-one derivative (1c) can be prepared by reacting $R^1$—Y, which was also used in (A), with the compound represented by the formula (3) in the presence of a base in a solvent.

Examples of the base usable in the reaction can include inorganic bases such as potassium carbonate and sodium carbonate and organic bases such as metal alkoxides. Usable examples of the solvent can include N,N-dimethylformamide, dimethylsulfoxide, acetone and methyl ethyl ketone. The reaction may be conducted preferably at 20 to 150° C. for 1 to 20 hours, notably at 50 to 130° C. for 2 to 10 hours.

(D) Preparation of a Compound (1d) in Which $R^2$ is a Carboxyl Group:

This carboxyl-substituted pyridazin-3-one derivative (1d) can be prepared by hydrolyzing the compound (1c) in the presence of a base, such as caustic soda or caustic potash, in a solvent in a manner known per se in the art.

(E) Preparation of a Compound (1e) in Which $R^2$ is a Substituted Carbamoyl Group This substituted-carbamoyl-substituted pyridazin-3-one derivative (1e) can be prepared by converting the compound (1d) at the carboxyl group thereof into a reactive derivative and then reacting it with a corresponding amine $R^3R^4NH$ in which $R^3$ and $R^4$ have the same meanings as defined above.

Examples of the reactive derivative at the carboxyl group can include acid halides and mixed acid anhydrides. Conversion into such an acid halide can be effected with oxalyl chloride, thionyl chloride, thionyl bromide or the like. Conversion into such a mixed acid anhydride, on the other hand, can be effected with acetic anhydride, pivalic anhydride, methanesulfonic anhydride, p-toluenesulfonyl chloride or the like. The synthesis reaction of the reactive derivative may be conducted preferably in the presence or absence of a base at −10 to 150° C. for 1 to 20 hours, especially at 0 to 130° C. for 1 to 10 hours in a solvent, for example, tetrahydrofuran, N,N-dimethylformamide, dimethylsulfoxide, pyridine, chloroform, methylene chloride, toluene or benzene.

(F) Preparation of a Compound (1f) in Which $R^2$ is a Hydroxymethyl Group

This hydroxymethyl-substituted pyridazin-3-one derivative (1f) can be prepared by reacting an alkyl halocarbonate compound, such as ethyl chlorocarbonate, with the compound (1d) in the presence of a base such as triethylamine in a solvent to form a mixed acid anhydride and then reacting sodium borohydride with the mixed acid anhydride.

Usable examples of the solvent can include tetrahydrofuran, dioxane, diethyl ether, and ethyl acetate. The reaction may be conducted preferably at −20 to 50° C. for 0.5 to 10 hours, notably at 0 to 30° C. for 0.5 to 3 hours.

(G) Preparation of a Compound (1g) in Which $R^2$ is a Halogenated Methyl Group This halogenated-methyl-substituted pyridazin-3-one derivative (1g) in which X is a chlorine atom: or bromine atom can be prepared by reacting a halogenating agent, such as thionyl chloride, thionyl bromide, phosphorus trichloride, phosphorus pentachloride or phosphorus tribromide, with the compound (1f) in a solvent. Further, the halogenated-methyl-substituted pyridazin-3-one derivative (1g) in which X is an iodine atom can be prepared by reacting sodium iodide, potassium iodide or the like with the above compound in a solvent.

Usable examples of the solvent for the halogenation (chlorination, bromination) can include benzene, toluene, tetrahydrofuran, dioxane, diethyl ether, ethyl acetate, and chloroform. The reaction may be conducted preferably at 20 to 130° C. for 0.5 to 5 hours, especially at 30 to 100° C. for 1 to 3 hours. In the preparation of the compound (1g) in which X is an iodine atom, acetone, methyl ethyl ketone, N,N-dimethylformamide, dimethyl sulfoxide, ethyl acetate, chloroform or the like can be used as the solvent. The reaction may be conducted preferably at 40 to 150° C. for 0.5 to 10 hours, notably at 50 to 120° C. for 1 to 5 hours.

(H) Preparation of a Compound (1h) in Which $R^2$ is a (Substituted) Phthalimidomethyl Group This compound (1h) which has a (substituted) phthalimidomethyl group at the 4-position can be prepared by reacting potassium phthalimide or substituted potassium phthalimide with the compound (1g) in a solvent.

Usable examples of the solvent can include N,N-dimethylformamide, dimethyl sulfoxide, tetrahydrofuran, dioxane, benzene, and toluene. The reaction may be conducted preferably at 50 to 150° C. for 0.5 to 5 hours, notably at 70 to 120° C. for 1 to 3 hours.

(I) Preparation of a Compound (1i) in Which $R^2$ is a (Lower Alkoxy)Carbonyl Group This (lower alkoxy)carbonyl-substituted pyridazin-3-one derivative (1i) can be prepared by reacting a lower alcohol $R^7$—OH, in which $R^7$ has the same meaning as defined above, with the reactive derivative of the compound (1d) at the carboxyl thereof, which was used in the preparation of the compound (1e), in the presence or absence of a base in a solvent such as tetrahydrofuran, N,N-dimethylformamide, dimethyl sulfoxide, ethyl acetate, pyridine, chloroform, methylene chloride, toluene or benzene. As an alternative process, it can also be prepared by a usual ester preparation process, namely, by reacting the lower alcohol $R^7$—OH with the compound (1d) in the presence of an acid catalyst in a solvent.

The intermediates and target compounds obtained in the above-described individual reactions can be separated and purified by purification methods commonly employed in organic synthesis chemistry, for example, by subjecting them to filtration, extraction, washing, drying, concentration, recrystallization, various chromatographic treatment, and the like. The intermediates may be provided for the next reactions without purifying them specifically. Further, they may also be obtained as solvates of solvents such as reaction solvents or recrystallization solvents, especially as hydrates.

The pyridazin-3-one derivatives (1) and their salts according to the present invention, which are available as described above, have excellent inhibitory activity against interleukin-1β production, and are useful as preventives or therapeutics for immune system diseases, inflammatory diseases, ischemic diseases, osteoporosis, ichorrhemia, rheumatism, arthritis and inflammatory colitis.

Medicines according to the present invention contain the pyridazin-3-one derivatives (1) or their salts as effective ingredients. Using them alone or together with pharmacologically-acceptable carriers such as solubilizers, excipients, binders or extenders, they can be formed into pharmaceutical preparation forms such as tablets, capsules, granules, powders, injections and suppositories. These pharmaceutical preparations can be produced by known methods. For example oral preparations can be produced by suitably formulating the pyridazin-3-one derivatives (1) or their salts in combination with solubilizers such as tragacanth gum, gum arabic, sucrose esters, lecithin, olive oil, soybean oil and PEG400; excipients such as starch, mannitol and lactose; binders such as carboxymethylcellulose sodium and hydroxypropylcellulose; disintegrators such as crystalline cellulose and carboxymethylcellulose calcium; lubricants such as talc and magnesium stearate; anticaking agents such as light anhydrous silicic acid.

The dosage of each medicine according to the present invention varies depending on the body weight, age, sex, conditions and the like. In general, however, it is preferred to orally or parenterally administer to an adult the medicine in an amount of about 0.01 to 1,000 mg, preferably 0.1 to 100 mg in terms of the compound represented by the formula (1) per day at once or in several portions.

EXAMPLES

The present invention will next be described in further detail by the following Examples. It should however be borne in mind that the present invention is not limited to these Examples.

Example 1

Preparation of 5,6-bis(4-Methoxyphenyl)-4-cyano-2-cyclopropylmethyl-2H-pyridazin-3-one (Chloromethyl)cyclopropane (0.6 ml, 6.36 mmol) was added to a solution of 5,6-bis(4-methoxyphenyl)-4-cyano- 2H-pyridazin-3-one (1.71 g, 5.10 mmol) and potassium carbonate (2.02 g, 14.62 mmol) in N,N-dimethylformamide (5 ml), followed by stirring at a bath temperature of 80° C. for 6 hours. Water was then added to the reaction mixture, followed by extraction with ethyl acetate (300 ml). The organic layer was washed with water and a saturated aqueous solution of sodium chloride (brine), successively, and was then dried over anhydrous sodium sulfate. The solvent was distilled off, whereby the title compound (1.413 g, 71.5%) was obtained as yellow crystals.
Pale yellow prisms (chloroform-diethyl ether).
Melting point: 175.6–176.1° C.
$^1$H-NMR (CDCl$_3$) δ:0.47–0.54(2H, m), 0.54–0.67(2H, m), 1.36–1.52(1H, m), 3.79(3H, s), 3.83(3H, s), 4.15(2H, d, J=7.33 Hz), 6.77(2H, d, J=9.04 Hz), 6.88(2H, d, J=9.04 Hz), 7.04(2H, d, J=9.04 Hz), 7.16(2H, d, J=9.03 Hz). IR (KBr) cm$^1$: 2235,1667,1608,1512,1255,1179,1024,837.

Example 2

Preparation of 5,6-bis(4-methoxyphenyl)-4-carbamoyl-2-cyclopropylmethyl-2H-pyridazin-3-one A 2 N aqueous solution of sodium hydroxide (4 ml) was added to a solution of 5,6-bis(4-methoxyphenyl)-4-cyano-2-cyclopropylmethyl-2H-pyridazin-2-one (171 mg, 0.44 mmol) in methanol (2 ml), followed by stirring at a bath temperature of 70° C. for 8 hours. A mixture of 2 N aqueous solution of sodium hydroxide (1 ml) and methanol (2 ml) was added further, followed by stirring at a bath temperature of 70° C. for 12 hours. After the methanol was distilled off, the residue was extracted with ethyl acetate. The extract was washed with water and brine, successively, and was then dried over anhydrous sodium sulfate. The solvent was distilled off. The residue (197 mg) was separated and purified by silica gel preparative chromatography [developer: chloroform/methanol (10/1)] and then crystallized from chloroform-diethyl ether-hexane, whereby the title compound (158 mg, 88.2%) was obtained as pale yellow prisms.
Melting point: 174.2–175.2° C.
$^1$H-NMR (CDCl$_3$) δ: 0.43–0.53 (2H, m), 0.53–0.66 (2H, m), 1.38–1.53 (1H, m), 3.77 (3H, s), 3.79 (3H, s), 4.13 (2H, d, J=7.33 Hz), 5.74 (1H, brs), 6.73 (2H, d, J=8.79 Hz), 6.79 (2H, d, J=8.79 Hz), 7.00 (2H, J=8.30 Hz), 7.05 (2H, J=8.31 Hz).
IR (KBr) cm$^1$: 3371,3331,3173,1682,1635,1610,1583,1252, 1177,1027,828.
Mass(m/z): 405 (M$^+$).

Example 3

Preparation of 5,6-bis(4-Methoxyphenyl)-4-cyano2-ethyl-2H-pyridazin-3-one

Using 5,6-bis(4-methoxyphenyl)-4-cyano-2H-pyridazin-3-one and ethyl iodide as starting materials, the procedures of Example 1 were repeated likewise, whereby the title compound was obtained in a yield of 76.8%.
Yellow prisms (ethyl acetate)
Melting point: 170.5–171.5° C.
$^1$H-NMR (CDCl$_3$) δ: 1.48 (3H, t, J=7.33 Hz), 3.79 (3H, s), 3.83 (3H, s), 4.35 (2H, q, J=7.33 Hz), 6.76 (2H, d, J=8.79 Hz), 6.88 (2H, d, J=9.03 Hz), 7.04 (2H, d, J=9.03 Hz), 7.15 (2H, d, J=9.03 Hz).
IR (KBr) cm$^{-1}$: 2232,1660,1602,1516,1255,1174,1024,840.
Mass (m/z): 361 (M$^+$).

Example 4

Preparation of 5,6-bis(4-Methoxyphenyl)-4-carbamoyl-2-ethyl-2H-pyridazin-3-one

Using 5,6-bis(4-methoxyphenyl)-4-cyano-2-ethyl-2H-pyridazin-3-one as a starting material, the procedures of Example 2 were repeated likewise, whereby the title compound was obtained in a yield of 69.8%.
Pale yellow prisms (chloroform-hexane)
Melting point: 226.2–227.5° C.
$^1$H-NMR (CDCl$_3$) δ: 1.47 (3H, t, J=7.32 Hz), 3.77 (3H, s), 3.79 (3H, s), 4.34 (2H, q, J=7.32 Hz), 5.69 (1H, brs), 6.73 (2H, d, J=8.79 Hz), 6.79 (2H, d, J=9.03 Hz), 6.9–7.05 (1H, br), 7.01 (2H, d, J=9.03 Hz), 7.02 (2H, d, J=9.0 Hz)
IR (KBr) cm$^{-1}$: 3428,3316,1660,1647,1610,1520,1512, 1249,1183,1026,839.

Example 5

Preparation of 5,6-bis(4-Methoxyphenyl)-4-cyano-2-n-propyl-2H-pyridazin-3-one

Using 5,6-bis(4-methoxyphenyl)-4-cyano-2H-pyridazin-3-one and 1-bromopropane as starting materials, the procedures of Example 1 were repeated likewise, whereby the title compound was obtained in a yield of 72.6%.
Pale yellow scales (ethyl acetate-diethyl ether)
Melting point: 151.4–151.9° C.
$^1$H-NMR (CDCl$_3$) δ: 1.03 (3H, t, J=7.6 Hz), 1.94 (2H, sext, J=7.6 Hz), 3.79 (3H, s), 3.80 (3H, s), 4.25 (2H, t, J=7.6 Hz), 6.77 (2H, d, J=9.0 Hz), 6.88 (2H, d, J=9.0 Hz), 7.03 (2H, d, J=9.0 Hz), 7.14 (2H, d, J=8.8 Hz).
IR (KBr) cm$^{-1}$: 1665,1608,1609,1512,1252,1178,834. Mass (m/z): 375 (M$^+$)

Example 6

Preparation of 5,6-bis(4-Methoxyphenyl)-4-carbamoyl-2-n-propyl-2H-pyridazin-3-one Using 5,6-bis(4-methoxyphenyl)-4-cyano-2-n-propyl-2H-pyridazin-3-one as a starting material, the procedures of Example 2 were repeated likewise, whereby the title compound was obtained in a yield of 67.6%.
Colorless needles (ethyl acetate-hexane)
Melting point: 167.3–180.4° C.
$^1$H-NMR (CDCl$_3$) δ: 1.03 (3H, t, J=7.6 Hz), 1.93 (2H, sext, J=7.6 Hz), 3.77 (3H, s), 3.79 (3H, s), 4.24 (2H, t, J=7.6 Hz), 5.69 (1H, br), 6.73 (2H, d, J=9.0 Hz), 6.79 (2H, d, J=8.8 Hz), 6.99 (2H, d, J=8.3 Hz), 7.02 (2H, d, J=8.5 Hz), 7.08 (1H, br).
IR (KBr) cm$^{-1}$: 3428,1675,1637,1611,1585,1516,1252, 1179. Mass (m/z): 393 (M$^+$).

Example 7

Preparation of 5,6-bis(4-Methoxyphenyl)-4-cyano-2-isopropyl-2H-pyridazin-3-one

Using 5,6-bis(4-methoxyphenyl)-4-cyano-2H-pyridazin-3-one and isopropyl chloride as starting materials, the procedures of Example 1 were repeated likewise, whereby the title compound was obtained in a yield of 72.6%.
Pale yellow crystals (ethyl acetate-diethyl ether)
Melting point: 196.7–197.6° C.
$^1$H-NMR (CDCl$_3$) δ: 1.46 (6H, d, J=6.6 Hz), 3.79 (3H, s), 3.84 (3H, s), 5.41 (1H, sept, J=6.6 Hz), 6.77 (2H, d, J=8.5 Hz), 6.89 (2H, d, J=8.5 Hz), 7.05 (2H, d, J=8.5 Hz), 7.17 (2H, d, J=8.5 Hz).
IR (KBr) cm$^{-1}$: 2118,1667,1609,1516,1383,1364,1254, 1180, 843. Mass (m/z): 375 (M$^+$).

Example 8

Preparation of 5,6-bis(4-Methoxyphenyl)-4-carbamoyl-2-isopropyl-2H-pyridazin-3-one Using 5,6-bis(4-methoxyphenyl)-4-cyano-2-isopropyl-2H-pyridazin-3-one as a starting material, the procedures of Example 2 were repeated likewise, whereby the title compound was obtained in a yield of 72.0%.
Slightly yellow needles (chloroform-ethyl acetatediethyl ether)
Melting point: 165.2–166.4° C.
$^1$H-NMR (CDCl$_3$) δ: 1.45 (6H, d, J=6.6 Hz), 3.78 (3H, s), 3.79 (3H, s), 5.41 (1H, sept, J=6.6 Hz), 5.66 (1H, br), 6.73 (2H, d, J=9.0 Hz), 6.80 (2H, d, J=8.8 Hz), 6.93 (1H, br), 7.01 (2H, d, J=8.8 Hz), 7.04 (2H, d, J=8.8 Hz).
IR (KBr) cm$^{-1}$: 3348,1681,1636,1610,1514,1384,1365, 1251, 1180,834.
Mass (m/z): 393 (M$^+$).

Example 9

Preparation of 5,6-bis(4-Methoxyphenyl)-2-n-butyl-4-cyano-2H-pyridazin-3-one

Using 5,6-bis(4-methoxyphenyl)-4-cyano-2H-pyridazin-3-one and n-butyl chloride as starting materials, the procedures of Example 1 were repeated likewise, whereby the title compound was obtained in a yield of 72.6%.
Pale yellow scales (ethyl acetate-diethyl ether)
Melting point: 134.4–135.5° C.
$^1$H-NMR (CDCl$_3$) δ: 0.99 (3H, t, J=7.6 Hz), 1.44 (2H, sext, J=7.6 Hz), 1.89 (2H, quint, J=7.6 Hz), 3.79 (3H, s), 3.83 (3H, s), 4.29 (2H, t, J=7.6 Hz), 6.77 (2H, d, J=8.8 Hz), 6.88 (2H, d, J=9.0 Hz), 7.03 (2H, d, J=8.8 Hz), 7.15 (1H, d, J=8.8 Hz).
IR (KBr) cm$^{-1}$: 2962,2934,2838,2223,1663,1607,1512, 1252,1178,836. Mass (m/z): 389 (M$^+$).

Example 10

Preparation of 5,6-bis(4-Methoxyphenyl)-2-n-butyl-4-carbamoyl-2H-pyridazin-3-one Using 5,6-bis(4-methoxyphenyl)-2-n-butyl-4-cyano-2H-pyridazin-3-one as a starting material, the procedures of Example 2 were repeated likewise, whereby the title compound was obtained in a yield of 75.3%.
Colorless needles (chloroform-diethyl ether)
Melting point: 201.0–201.8° C.
$^1$H-NMR (CDCl$_3$) δ: 0.99 (3H, t, J=7.6 Hz), 1.45 (2H, sext, J=7.6 Hz), 1.88 (2H, quint, J=7.6 Hz), 3.77 (3H, s), 3.79 (3H, s), 4.28 (2H, t, J=7.6 Hz), 5.70 (1H, br), 6.73 (2H, d, J=8.8 Hz), 6.79 (2H, d, J=8.8 Hz), 7.00 (2H, d, J=8.3 Hz), 7.01 (2H, d, J=8.8 Hz), 7.08 (1H, br).
IR (KBr) cm$^{-1}$: 3427,1688,1631,1610,1515,1253,1179,833. Mass (m/z): 407 (M$^+$).

Example 11

Preparation of 5,6-bis(4-Methoxyphenyl)-4-cyano-2-isobutyl-2H-pyridazin-3-one

Using 5,6-bis(4-methoxyphenyl)-4-cyano-2H-pyridazin-3-one and isobutyl chloride as starting materials, the procedures of Example 1 were repeated likewise, whereby the title compound was obtained in a yield of 71.8%.
Pale yellow scales (ethyl acetate-hexane)
$^1$H-NMR (CDCl$_3$) δ: 1.02 (6H, d, J=6.6 Hz), 2.37 (1H, sept, J=6.8 Hz), 3.79 (3H, s), 3.83 (3H, s), 4.12 (2H, d, J=7.3 Hz), 6.77 (2H, d, J=9.0 Hz), 6.88 (2H, d, J=8.8 Hz), 7.03 (2H, d, J=8.8 Hz), 7.16 (2H, d, J=8.8 Hz).
IR (KBr) cm$^{-1}$: 2227,1664,1607,1383,1363,1256,1180,834. Mass (m/z): 389 (M$^+$).

Example 12

Preparation of 5,6-bis(4-Methoxyphenyl)-4-carbamoyl-2-isobutyl-2H-pyridazin-3-one Using 5,6-bis(4-methoxyphenyl)-4-cyano-2-isobutyl-2H-pyridazin-3-one as a starting material, the procedures of Example 2 were repeated likewise, whereby the title compound was obtained in a yield of 61.9%.
Colorless needles (ethyl acetate-diethyl ether)
Melting point: 156.5–157.2° C.
$^1$H-NMR (CDCl$_3$) δ: 1.02 (6H, d, J=6.8 Hz), 2.38 (1H, sept, J=6.8 Hz), 3.77 (3H, s,), 3.79 (3H, s), 4.11 (2H, d, J=7.3 Hz), 5.71 (1H, br), 6.73 (2H, d, J=9.0 Hz), 6.79 (2H, d, J=8.8 Hz), 6.99 (2H, d, J=9.0 Hz), 7.04 (2H, d, J=9.0 Hz), 7.12 (1H, br).
IR (KBr) cm$^{-1}$: 3410,1685,1641,1611,1512,1255,1178,830.
Mass (m/z): 407 (M$^+$)

Example 13

Preparation of 5,6-bis(4-Methoxyphenyl)-4-cyano-2-cyclopentylmethyl-2H-pyridazin-3-one Using 5,6-bis(4-methoxyphenyl)-4-cyano-2H-pyridazin-3-one and cyclopentylmethyl chloride as starting materials, the procedures of Example 1 were repeated likewise, whereby the title compound was obtained in a yield of 42.4%.
Yellow needles (ethyl acetate-diethyl ether)
Melting point: 180.2–180.7° C.
1H-NMR (CDCl$_3$) δ: 1.36–1.44 (2H, m), 1.56–1.81 (6H, m), 2.56 (1H, sept, J=7.6 Hz), 3.79 (3H, s), 3.83 (3H, s), 4.24 (2H, d, J=7.6 Hz), 6.77 (2H, d, J=8.8 Hz), 6.88 (2H, d, J=8.8 Hz), 7.03 (2H, d, J=8.8 Hz), 7.16 (2H, d, J=8.8 Hz).
IR (KBr) cm$^{-1}$: 2221,1655,1607,1512,1254,1175,835. Mass (m/z): 415 (M$^+$).

Example 14

Preparation of 5,6-bis(4-Methoxyphenyl)-4-carbamoyl-2-cyclopentylmethyl-2H-pyridazin-3-one Using 5,6-bis(4-methoxyphenyl)-4-cyano-2-cyclopentylmethyl-2H-pyridazin-3-one as a starting material, the procedures of Example 2 were repeated likewise, whereby the title compound was obtained in a yield of 81.1%.
Slightly yellow needles (chloroform-diethyl ether)
Melting point: 183.8–184.6° C.
$^1$H-NMR (CDCl$_3$) δ: 1.19–1.82 (8H, m), 2.59 (1H, sept, J=7.6 Hz), 3.77 (3H, s), 3.79 (3H, s), 4.23 (2H, d, J=7.6 Hz), 5.68 (1H, br), 6.73 (2H, d, J=8.8 Hz), 6.79 (2H, d, J=8.8 Hz), 6.99 (2H, d, J=8.5 Hz), 7.02 (2H, d, J=8.5 Hz), 7.12 (1H, br).
IR (KBr) cm$^1$: 3432,1688,1631,1610,1515,1254,1178,830.
Mass (m/z): 433 (M$^+$).

Example 15

Preparation of 5,6-bis(4-methoxyphenyl)-4-cyano-2-cyclohexylmethyl-2H-pyridazin-3-one Using 5,6-bis(4-methoxyphenyl)-4-cyano-2H-pyridazin-3-one and cyclohexylmethyl chloride as starting materials, the procedures of Example 1 were repeated likewise, whereby the title compound was obtained in a yield of 45.0%.
Yellow needles (chloroform-ethyl acetate)
Melting point: 185.0–186.8° C.
$^1$H-NMR (CDCl$_3$) δ: 1.05–1.33 (5H, m), 1.65–1.80 (5H, m), 2.00–2.12 (1H, m), 3.79 (3H, s), 3.83 (3H, s), 4.14 (2H, d, J=7.3 Hz), 6.77 (2H, d, J=9.0 Hz), 6.88 (2H, d, J=9.0 Hz), 7.03 (2H, d, J=8.8 Hz), 7.16 (2H, d, J=9.0 Hz).
IR (KBr) cm$^{-1}$: 2223,1658,1607,1512,1254,1175,835. Mass (m/z): 429 (M$^+$).

Example 16

Preparation of 5,6-bis(4-Methoxyphenyl)-4-carbamoyl-2-cyclhexylmethyl-2H-pyridazin-3-one Using 5,6-bis(4-methoxyphenyl)-4-cyano-2-cyclohexylmethyl-2H-pyridazin-3-one as a starting material, the procedures of Example 2 were repeated likewise, whereby the title compound was obtained in a yield of 80.3%.
Colorless needles (ethyl acetate-hexane)
Melting point: 183.9–184.5° C.
$^1$H-NMR (CDCl$_3$) δ: 1.06–1.32 (5H, m), 1.55–1.76 (5H, m), 2.03–2.08 (1H, m), 3.77 (3H, s), 3.79 (3H, s), 4.12 (2H, d, J=7.3 Hz), 5.69 (1H, br), 6.73 (2H, d, J=8.8 Hz), 6.79 (2H, d, J=8.5 Hz), 6.99 (2H, d, J=8.5 Hz), 7.02 (2H, d, J=8.5 Hz), 7.12 (1H, br).
IR (KBr) cm$^{-1}$: 3432,1690,1629,1609,1515,1253,1177,830. Mass (m/z): 447 (M$^+$).

Example 17

Preparation of 2-Benzyl-5,6-bis(4-methoxyphenyl)-4-cyano-2H-pyridazin-3-one

Using 5,6-bis(4-methoxyphenyl)-4-cyano-2H-pyridazin-3-one and benzyl chloride as starting materials, the procedures of Example 1 were repeated likewise, whereby the title compound was obtained in a yield of 65.4%.
Orange needles (chloroform-diethyl ether)
Melting point: 178.8–179.2° C.
$^1$H-NMR (CDCl$_3$) δ: 3.79 (3H, s), 3.82 (3H, s), 5.43 (2H, s), 6.76 (2H, d, J=9.0 Hz), 6.86 (2H, d, J=9.0 Hz), 7.01 (2H, d, J=8.8 Hz), 7.12 (2H, d, J=9.0 Hz), 7.32–7.40 (3H, m), 7.55–7.58 (2H, m).
IR (KBr) cm$^{-1}$: 2228,1662,1609,1513,1253,1179,836. Mass (m/z): 423 (M$^+$).

Example 18

Preparation of 2-Benzyl-5,6-bis(4-methoxyphenyl)-4-carbamoyl-2H-pyridazin-3-one

Using 2-benzyl-5,6-bis(4-methoxyphenyl)-4-cyano-2H-pyridazin-3-one as a starting material, the procedures of Example 2 were repeated likewise, whereby the title compound was obtained in a yield of 67.7%.
Colorless powder (chloroform-ethyl acetate)
Melting point: 192.9–193.7° C.
$^1$H-NMR (CDCl$_3$) δ: 3.77 (3H, s), 3.78 (3H, s), 5.43 (2H, s), 5.62 (1H, br), 6.73 (2H, d, J=9.0 Hz), 6.78 (2H, d, J=8.8 Hz), 6.93 (1H, br), 6.99 (4H, d, J=8.8 Hz), 7.30–7.40 (3H, m), 7.54–7.56 (2H, m).
IR (KBr) cm$^{-1}$: 3402,1676,1640,1611,1513,1255,1179,834. Mass (m/z): 441 (M$^+$).

Example 19

Preparation of 5,6-bis(4-Methoxyphenyl)-4-ethoxy-carbonyl-2H-pyridazin-3-one

Potassium carbonate (2.72 g) and isobutyl bromide (1.08 g) were added to a solution of 5,6-bis(4-methoxyphenyl)-4-ethoxycarbonyl-2H-pyridazin-3-one (1.50 g, 3.94 mmol) in N,N-dimethylformamide (15 ml), followed by stirring at 80° C. for 4 hours. After the reaction mixture was concentrated, water was added, followed by extraction with ethyl acetate. The extract was dried over anhydrous sodium carbonate, the solvent was distilled off under reduced pressure, and the residue was then crystallized from ethyl acetatehexane, whereby the title compound (1.54 g, 89.4%) was obtained as colorless prisms.
Melting point: 134.3–134.7° C.
$^1$H-NMR (CDCl$_3$) δ: 1.02 (6H, d, J=6.6 Hz), 1.09 (3H, t, J=7.1 Hz), 2.39 (1H, nonet, J=6.8 Hz), 3.77 (3H, s), 3.79 (3H, s), 4.09 (2H, d, J=7.3 Hz), 4.17 (2H, q, J=7.1 Hz), 6.74 (2H, d, J=8.8 Hz), 6.79 (2H, d, J=8.8 Hz), 7.03 (2H, d, J=8.8 Hz), 7.04 (2H, d, J=8.8 Hz).
IR (KBr) cm$^1$: 1732,1651,1610,1516,1293,1253,1183,1027, 841. Mass (m/z): 436 (M$^+$).

Example 20

Preparation of 5,6-bis(4-Methoxyphenyl)-4-carboxy-2-isobutyl-2H-pyridazin-3-one

A 2 N aqueous solution of sodium hydroxide (50 ml) was added to a solution of 5,6-bis(4-methoxyphenyl)-4-ethoxycarbonyl-2-isobutyl-2H-pyridazin-3-one (1.4 g, 3.21 mmol) in ethanol (50 ml), followed by heating under reflux for 3 hours. Ethanol was distilled off under reduced pressure, and hydrochloric acid was added to the residue to neutralize the same. Precipitated crystals were collected by filtration and then recrystallized from ethanol-hexane, whereby the title compound (1.07 g, 81.3%) was obtained as yellow prisms.
Melting point: 186.5–187.0° C.
$^1$H-NMR (CDCl$_3$) δ: 1.06 (6H, d, J=7.1 Hz), 2.41 (1H, nonet, J=7.1 Hz), 3.77 (3H, s), 3.80 (3H, s), 4.20 (2H, d, J=7.1 Hz), 6.73 (2H, d, J=8.8 Hz), 6.81 (2H, d, J=8.8 Hz), 6.92–6.98 (4H, m).
IR (KBr) cm$^1$: 1745,1610,1578,1561,1514,1464,1292,1252, 1180,1027,834. Mass (m/z): 408 (M$^+$).

Example 21

Preparation of 5,6-bis(4-Methoxyphenyl)-2-isobutyl-4-methylcarbamoyl-2H-pyridazin-3-one p-Toluenesulfonyl chloride (84 mg) was added to a solution of 5,6-bis(4-methoxyphenyl)-4-carboxy-2-isobutyl-2H-pyridazin-3-one (150 mg, 0.37 mmol) in pyridine (5 ml), followed by stirring at room temperature for 30 minutes. Methylamine hydrochloride (124 mg) was then added, and the mixture was stirred overnight. Water was added to the reaction mixture, followed by extraction with chloroform. The extract was dried over anhydrous sodium sulfate, the solvent was distilled off under reduced pressure, and the residue was then separated and purified by chromatography on a silica gel column. Crystallization was conducted from chloroform-hexane, whereby the title compound (76.4 mg, 49.4%) was obtained as slightly yellow needles.
Melting point: 88.9–89.7° C.
$^1$H-NMR (CDCl$_3$) δ: 1.01 (6H, d, J=6.6 Hz), 2.36 (1H, sept, J=6.8 Hz), 2.82 (3H, d, J=4.9 Hz), 3.77 (3H, s), 3.78 (3H, s), 4.09 (2H, d, J=7.3 Hz), 6.72 (2H, d, J=8.5 Hz), 6.78 (2H, d, J=8.5 Hz), 6.98 (2H, d, J=8.5 Hz), 6.99 (2H, d, J=8.5 Hz), 7.32 (1H, brq, J=4.9 Hz).
IR (KBr) cm$^1$: 1629,1611,1515,1292,1251,1179,1030. Mass (m/z): 421 (M$^+$)

Example 22

Preparation of 5,6-bis(4-Methoxyphenyl)-4-dimethyl-carbamoyl-2-isobutyl-2H-pyridazin-3-one Thionyl chloride (43.7 mg) was added to a solution of 5,6-bis(4-methoxyphenyl)-4-carboxy-2-isobutyl-2H-pyridazin-3-one (100 mg, 0.24 mmol) in benzene (5 ml), followed by stirring at 75° C. for 2 hours. The reaction mixture was distilled under reduced pressure. Benzene (5 ml) and dimethylamine hydrochloride (100 mg) were added to the residue, and the mixture was then heated overnight under reflux. Water was added to the reaction mixture, followed by extraction with ethyl acetate. The extract was washed with water and then dried over anhydrous sodium sulfate. The solvent was distilled off under reduced pressure. The residue was separated and purified by silica gel preparative chromatography [developer: ethyl acetate] and was then crystallized from chloroform-hexane, whereby the title compound was quantitatively obtained as colorless needles.
Melting point: 188.6–189.2° C.
$^1$H-NMR (CDCl$_3$) δ: 1.00 (3H, d, J=6.6 Hz), 1.03 (3H, d, J=6.6 Hz), 2.31–2.46 (1H, m), 2.72 (3H, s), 2.88 (3H, s), 3.77 (3H, s), 3.79 (3H, s), 4.08 (1H, dd, J=12.4,7.1 Hz), 4.10 (1H, dd, J=12.4,7.6 Hz), 6.74 (2H, d, J=9.0 Hz), 6.78 (2H, d, J=9.0 Hz), 7.00–7.14 (4H, m).
IR (KBr) cm$^{-1}$: 1645,1609,1513,1466,1309,1302,1291,1251, 1183,1027. Mass (m/z): 435 (M$^+$).

Example 23

Preparation of 5,6-bis(4-Methoxyphenyl)-2-isobutyl-4-phenylcarbamoyl-2H-pyridazin-3-one Using 5,6-bis(4-methoxyphenyl)-4-carboxy-2-isobutyl-2H-pyridazin-3-one and aniline as starting materials, the procedures of Example 22 were repeated likewise, whereby the title compound was obtained in a yield of 89.0%.
Pale yellow needles (chloroform-hexane)
Melting point: 105.5–106.2° C.
$^1$H-NMR (CDCl3) δ: 1.02 (6H, d, J=6.8 Hz), 2.39 (1H, sept, J=6.8 Hz), 3.77 (3H, s), 3.78 (3H, s), 4.10 (2H, d, J=7.1 Hz), 6.74 (2H, d, J=8.8 Hz), 6.78 (2H, d, J=8.8 Hz), 6.98 (2H, d, J=8.8 Hz), 7.03 (2H, d, J=8.8 Hz), 7.19–7.27 (3H, m), 7.50 (2H, d, J=7.6 Hz), 10.00 (1H, brs).
IR (KBr) cm$^{-1}$: 1624,1610,1582,1552,1516,1500,1444, 1292, 1253,1179,1030. Mass (m/z): 483 (M$^+$).

Example 24

Preparation of 5,6-bis(4-Methoxyphenyl)-2-isobutyl-4-(4-pyridylcarbamoyl)-2H-pyridazin-3-one Using 5,6-bis(4-methoxyphenyl)-4-carboxy-2-isobutyl-2H-pyridazin-3-one and 4-aminopyridine as starting materials, the procedures of Example 22 were repeated likewise, whereby the title compound was obtained quantitatively.
Colorless prisms (chloroform-hexane)
Melting point: 200.7–201.1° C.
$^1$H-NMR (CDCl$_3$) δ: 1.01 (6H, d, J=6.6 Hz), 2.28–2.43 (1H, m), 3.778 (3H, s), 3.784 (3H, s), 4.04 (2H, d, J=7.3 Hz), 6.74 (2H, d, J=8.8 Hz), 6.80 (2H, d, J=8.8 Hz), 6.98 (2H, d, J=8.8 Hz), 7.01 (2H, d, J=8.8 Hz), 7.42 (2H, d, J=6.3 Hz), 8.36 (2H, d, J=6.3 Hz), 10.81 (1H, brs).
IR (KBr) cm$^{-1}$: 1701,1610,1594,1516,1337,1292,1252, 1179,1032,832. Mass (m/z): 484 (M$^+$).

Example 25

Preparation of 5,6-bis(4-Methoxyphenyl)-4-ethoxycarbonyl-2-isopropyl-2H-pyridazin-3-one Using 5,6-bis(4-methoxyphenyl)-4-ethoxycarbonyl-2H-pyridazin-3-one and isopropyl bromide as starting materials, the procedures of Example 19 were repeated likewise, whereby the title compound was obtained in a yield of 92.3%.
Colorless prisms (chloroform-hexane)
Melting point: 163.0–163.2° C.
$^1$H-NMR (CDCl$_3$) δ: 1.08 (3H, t, J=7.1 Hz), 1.44 (6H, d, J=6.6 Hz), 3.78 (3H, s), 3.80 (3H, s), 4.17 (2H, q, J=7.1 Hz), 5.35–5.46 (1H, m), 6.74 (2H, d, J=8.8 Hz), 6.80 (2H, d, J=8.8 Hz), 7.05 (2H, d, J=8.8 Hz), 7.06 (2H, d, J=8.8 Hz).

IR (KBr) cm$^{-1}$: 2974,2938,1732,1645,1611,1516,1254, 1029, 840. Mass (m/z): 422 (M$^+$).

Example 26

Preparation of 5,6-bis(4-methoxyphenyl)-4-carboxy-2-isopropyl-2H-pyridazin-3-one Using 5,6-bis(4-methoxyphenyl)-4-ethoxycarbonyl-2-isopropyl-2H-pyridazin-3-one as a starting material, the procedures of Example 20 were repeated likewise, whereby the title compound was obtained in a yield of 97.9%.
Slightly yellow prisms (chloroform-hexane)
Melting point: 213.7–214.9° C. (dec.)
$^1$H-NMR (CDCl$_3$) δ: 1.50 (6H, d, J=6.8 Hz), 3.78 (3H, s), 3.80 (3H, s), 5.40–5.51 (1H, m), 6.73 (2H, d, J=8.8 Hz), 6.82 (2H, d, J=8.8 Hz), 6.95 (2H, d, J=8.8 Hz), 6.97 (2H, d, J=8.8 Hz), 14.50 (1H, br).
IR (KBr) cm$^{-1}$: 1740,1610,1560,1514,1251,1178. Mass (m/z): 394 (M$^+$).

Example 27

Preparation of 5,6-bis(4-Methoxyphenyl)-2-isopropyl-4-methylcarbamoyl-2H-pyridazin-3-one Using 5,6-bis(4-methoxyphenyl)-4-carboxy-2-isopropyl-2H-pyridazin-3-one and methylamine hydrochloride as starting materials, the procedures of Example 22 were repeated likewise, whereby the title compound was obtained in a yield of 92.3%.
Colorless prisms (chloroform-hexane)
Melting point: 244.6–245.7° C.
$^1$H-NMR (CDCl$_3$) δ: 1.44 (6H, d, J=6.6 Hz), 2.81 (3H, d, J=4.9 Hz), 3.77 (3H, s), 3.79 (3H, s), 5.34–5.45 (1H, m), 6.73 (2H, d, J=8.8 Hz), 6.78 (2H, d, J=8.8 Hz), 6.96–7.04 (5H, m) [7.009 (2H, d, J=8.8 Hz), 7.014 (2H, d, J=8.8 Hz), and 1H, br].
IR (KBr) cm$^{-1}$: 3302,1660,1625,1610,1585,1512,1251, 1177.

Example 28

Preparation of 5,6-bis(4-Methoxyphenyl)-2-cyclopropylmethyl-4-ethoxycarbonyl-2H-pyridazin-3-one Using 5,6-bis(4-methoxyphenyl)-4-ethoxycarbonyl-2H-pyridazin-3-one and (chloromethyl)cyclopropane as starting materials, the procedures of Example 19 were repeated likewise, whereby the title compound was obtained in a yield of 89.1%.
Colorless needles (ethyl acetate-hexane)
Melting point: 149.9–150.7° C.
$^1$H-NMR (CDCl$_3$) δ: 0.46–0.53 (2H, m), 0.55–0.62 (2H, m), 1.08 (3H, t, J=7.1 Hz), 1.47 (1H, ttt, J=7.8,7.6,4.9 Hz), 3.77 (3H, s), 3.79 (3H, s), 4.12 (2H, d, J=7.6 Hz), 4.17 (2H, q, J=7.1 Hz), 6.74 (2H, d, J=9.0 Hz), 6.80 (2H, d, J=9.0 Hz), 7.03–7.07 (4H, m).
IR (KBr) cm$^{-1}$: 1734,1648,1516,1293,1254,1183,1026,843. Mass (m/z): 434 (M$^+$).

Example 29

Preparation of 5,6-bis(4-Methoxyphenyl)-4-carboxy-2-cyclopropylmethyl-2H-pyridazin-3-one Using 5,6-bis(4-methoxyphenyl)-2-cyclopropylmethyl-4-ethoxycarbonyl-2H-pyridazin-3-one as a starting material, the procedures of Example 20 were repeated likewise, whereby the title compound was obtained quantitatively.

Pale yellow prisms (chloroform-hexane)
Melting point: 196.5–197.8° C.
¹H-NMR (CDCl₃) δ: 0.46–0.56 (2H, m), 0.58–0.68 (2H, m), 1.49 (1H, ttt, J=7.8, 7.6, 4.6 Hz), 3.76 (3H, s), 3.79 (3H, s), 4.22 (2H, d, J=7.6 Hz), 6.73 (2H, d, J=8.8 Hz), 6.81 (2H, d, J=8.8 Hz), 6.97 (4H, d, J=8.8 Hz).
IR (KBr) cm⁻¹: 1738,1646,1610,1582,1563,1515,1465, 1291,1252,1180. Mass (m/z): 406 (M⁺)

Example 30

Preparation of 5,6-bis(4-Methoxyphenyl)-2-cyclopropylmethyl-4-methylcarbamoyl-2H-pyridazin-3-one Using 5,6-bis(4-methoxyphenyl)-4-carboxy-2-cyclopropylmethyl-2H-pyridazin-3-one and methylamine hydrochloride as starting materials, the procedures of Example 22 were repeated likewise, whereby the title compound was obtained in a yield of 88.2%.
Pale yellow prisms (chloroform-hexane)
Melting point: 195.8–196.3° C.
¹H-NMR (CDCl) δ: 0.42–0.50 (2H, m), 0.53–0.61 (2H, m), 1.44 (1H, ttt, J=8.1,7.3,4.9 Hz), 2.81 (3H, d, J=4.9 Hz), 3.77 (3H, s), 3.78 (3H, s), 4.10 (2H, d, J=7.3 Hz), 6.73 (2H, d, J=9.0 Hz), 6.78 (2H, d, J=9.0 Hz), 6.99 (2H, d, J=9.0 Hz), 7.01 (2H, d, J=9.0 Hz), 7.22 (1H, br).
IR (KBr) cm⁻¹: 1664,1629,1610,1583,1513,1292,1252, 1179,1030,835.
Mass (m/z): 419 (M⁺).

Example 31

Preparation of 4-Benzylcarbamoyl-5,6-bis(4-methoxyphenyl)-2-cyclopropylmethyl-2H-pyridazin-3-one Using 5,6-bis(4-methoxyphenyl)-4-carboxy-2-cyclopropylmethyl-2H-pyridazin-3-one and benzylamine as starting materials, the procedures of Example 22 were repeated likewise, whereby the title compound was obtained quantitatively.
Slightly yellow needles (chloroform-hexane)
Melting point: 166.9–167.5° C.
¹H-NMR (CDCl₃) δ: 0.46–0.52 (2H, m), 0.53–0.61 (2H, m), 1.46 (1H, ttt, J=7.8, 7.6, 4.9 Hz), 3.76 (3H, s), 3.80 (3H, s), 4.12 (2H, d, J=7.6 Hz), 4.47 (2H, d, J=5.9 Hz), 6.73 (2H, d, J=8.8 Hz), 6.77 (2H, d, J=8.8 Hz), 6.98–7.05 (7H, m), 7.20–7.25 (3H, m).
IR (KBr) cm⁻¹: 1645,1610,1586,1515,1455,1292,1252, 1179,1029,834.
Mass (m/z): 495 (M⁺).

Example 32

Preparation of 5,6-bis(4-Methoxyphenyl)-2-cyclopropylmethyl-4-(2-pyridylmethylcarbamoyl)-2H-pyridazin-3-one Using 5,6-bis(4-methoxyphenyl)-4-carboxy-2-cyclopropylmethyl-2H-pyridazin-3-one and 2-(aminomethyl)pyridine as starting materials, the procedures of Example 22 were repeated likewise, whereby the title compound was obtained quantitatively.
Slightly yellow needles (chloroform-hexane)
Melting point: 205.2–205.7° C.
¹H-NMR (CDCl₃) δ: 0.45–0.52 (2H, m), 0.53–0.62 (2H, m), 1.48 (1H, ttt, J=7.8,7.6,4.9 Hz), 3.74 (3H, s), 3.77 (3H, s), 4.14 (2H, d, J=7.6 Hz), 4.58 (2H, d, J=5.4 Hz), 6.70 (2H, d, J=8.8 Hz), 6.73 (2H, d, J=8.8 Hz), 7.01 (2H, d, J=8.8 Hz), 7.03 (2H, d, J=8.8 Hz), 7.09–7.15 (2H, m), 7.57 (1H, ddd, J=7.8, 7.6, 1.7 Hz), 7.62 (1H, brt, J=5.4 Hz), 8.45 (1H, ddd, J=4.9, 1.7, 1.0 Hz).
IR (KBr) cm⁻¹: 1661,1639,1611,1572,1517,1253,1180.
Mass (m/z): 496 (M⁺).

Example 33

Preparation of 2-Benzyl-5,6-bis(4-methoxyphenyl)-4-ethoxycarbonyl-2H-pyridazin-3-one Using 5,6-bis(4-methoxyphenyl)-4-ethoxycarbonyl-2H-pyridazin-3-one and benzyl chloride as starting materials, the procedures of Example 19 were repeated likewise, whereby the title compound was obtained in a yield of 99.1%.
Colorless prisms (chloroform-hexane)
Melting point: 159.4–159.9° C.
¹H-NMR (CDCl₃) δ: 1.06 (3H, t, J=7.1 Hz), 3.77 (3H, s), 3.78 (3H, s), 4.15 (2H, q, J=7.1 Hz), 5.41 (2H, s), 6.74 (2H, d, J=8.8 Hz), 6.78 (2H, d, J=8.8 Hz), 7.01 (2H, d, J=8.8 Hz), 7.02 (2H, d, J=8.8 Hz), 7.29–7.40 (3H, m), 7.54–7.60 (2H, m).
IR (KBr) cm⁻¹: 1739,1652,1609,1514,1318,1287,1251, 1227, 1184,1143,1029,837.
Mass (m/z): 470 (M⁺)

Example 34

Preparation of 2-Benzyl-5,6-bis(4-methoxyphenyl)-4-carboxy-2H-pyridazin-3-one

Using 2-benzyl-5,6-bis(4-methoxyphenyl)-4-ethoxycarbonyl-2H-pyridazin-3-one as a starting material, the procedures of Example 20 were repeated likewise, whereby the title compound was obtained in a yield of 89.4%.
Yellow prisms (chloroform-methanol-hexane)
Melting point: 192.0–192.9° C.
¹H-NMR (CDCl₃) δ: 3.47 (1H, s), 3.77 (3H, s), 3.78 (3H, s), 5.50 (2H, s), 6.73 (2H, d, J=8.8 Hz), 6.79 (2H, d, J=8.8 Hz), 6.92 (2H, d, J=8.8 Hz), 6.94 (2H, d, J=8.8 Hz), 7.33–7.42 (3H, m), 7.55 (2H, dd, J=7.8,1.7 Hz).
IR (KBr) cm⁻¹: 1744,1611,1559,1514,1292,1253,1183, 1028. Mass (m/z): 442 (M⁺).

Example 35

Preparation of 2-Benzyl-5,6-bis(4-methoxyphenyl)-4-methylcarbamoyl-2H-pyridazin-3-one Using 2-benzyl-5,6-bis(4-methoxyphenyl)-4-carboxy-2H-pyridazin-3-one and methylamine hydrochloride as starting materials, the procedures of Example 22 were repeated likewise, whereby the title compound was obtained in a yield of 90.9%.
Slightly yellow prisms (chloroform-hexane)
Melting point: 183.5–184.30° C.
¹H-NMR (CDCl₃) δ: 2.78 (3H, d, J=4.9 Hz), 3.76 (3H, s), 3.77 (3H, s), 5.40 (2H, s), 6.72 (2H, d, J=8.8 Hz), 6.76 (2H, d, J=8.8 Hz), 6.97 (2H, d, J=8.8 Hz), 6.98 (2H, d, J=8.8 Hz), 7.07 (1H, brd, J=4.9 Hz), 7.28–7.38 (3H, m), 7.53 (2H, dd, J=8.1, 1.5 Hz).
IR (KBr) cm⁻¹: 1654,1636,1610,1515,1293,1250,1179,834.
Mass (m/z): 455 (M⁺).

Example 36

Preparation of 2-Benzyl-5,6-bis(4-methoxyphenyl)-4-ethylcarbamoyl-2H-pyridazin-3-one Using 2-benzyl-5,6-bis(4-methoxyphenyl)-4-carboxy-2H-pyridazin-3-one and ethylamine hydrochloride as starting materials, the procedures of Example 22 were repeated likewise, whereby the title compound was obtained in a yield of 59.0%.
Colorless needles (chloroform-hexane)
Melting point: 187.2–187.8° C.
$^1$H-NMR (CDCl$_3$) δ: 0.99 (3H, t, J=7.3 Hz), 3.24 (2H, dq, J=7.3, 5.9 Hz), 3.76 (3H, s), 3.77 (3H, s), 5.40 (2H, s), 6.68–6.80 (5H, m), 6.988 (2H, d, J=8.8 Hz), 6.990 (2H, d, J=8.8 Hz), 7.28–7.38 (3H, m), 7.53 (2H, dd, J=8.1, 1.5 Hz).
IR (KBr) cm$^{-1}$: 1682,1659,1643,1633,1610,1563,1514, 1289, 1254,1182,1029,842,701.
Mass (m/z): 469 (M$^+$).

Example 37

Preparation of 2-Benzyl-5,6-bis(4-Methoxyphenyl)-4-dimethylcarbamoyl-2H-pyridazin-3-one Using 2-benzyl-5,6-bis(4-methoxyphenyl)-4-carboxy-2H-pyridazin-3-one and dimethylamine hydrochloride as starting materials, the procedures of Example 22 were repeated likewise, whereby the title compound was obtained in a yield of 42.1%.
Pale yellow prisms (chloroform-hexane)
Melting point: 176.9–177.2° C.
$^1$H-NMR (CDCl$_3$) δ: 2.67 (3H, s), 2.87 (3H, s), 3.77 (3H, s), 3.78 (3H, s), 5.38 (1H, d, J=13.4 Hz), 5.43 (1H, d, J=13.4 Hz), 6.74 (2H, d, J=9.0 Hz), 6.76 (2H, d, J=9.0 Hz), 7.04 (4H, d, J=9.0 Hz), 7.28–7.38 (3H, m), 7.56 (2H, dt, J=8.3, 2.0 Hz).
IR (KBr) cm$^{-1}$: 1645,1609,1512,1302,1293,1253,1181, 1026, 838.
Mass (m/z): 469 (M$^+$).

Example 38

Preparation of 5,6-bis(4-Methoxyphenyl)-4-hydroxymethyl-2-isobutyl-2H-pyridazin-3-one Triethylamine (278.7 mg) and ethyl chlorocarbonate (298.9 mg) were added under ice cooling to a solution of 5,6-bis(4-methoxyphenyl)-4-carboxy-2-isobutyl-2H-pyridazin-3-one (750 mg, 1.84 mmol) in tetrahydrofuran (8 ml), followed by stirring for 1 hour. The reaction mixture was filtered. Under ice cooling, sodium borohydride (277.8 mg) was added to the filtrate, followed by stirring for 1 hour. The mixture was stirred further at room temperature for 2 hours. The reaction mixture was concentrated, to which a saturated aqueous solution of ammonium chloride was added. After the mixture was extracted with ethyl acetate, the extract was washed with a saturated aqueous solution of sodium hydrogencarbonate and water, successively, and was the dried over anhydrous sodium sulfate. The solvent was distilled off under reduced pressure. The residue was separated and purified by chromatography on a silica gel column and then crystallized from ethyl acetate-hexane, whereby the title compound (383.0 mg, yield: 52.9%) was obtained as colorless needles.
Melting point: 121.4–122.1° C.
$^1$H-NMR (CDCl$_3$) δ: 1.03 (6H, d, J=6.8 Hz), 2.32–2.47 (1H, m), 3.76 (3H, s), 3.80 (3H, s), 4.11 (2H, d, J=7.3 Hz), 4.39 (1H, dt, J=6.6, 1.2 Hz), 4.51 (2H, d, J=6.6 Hz), 6.72 (2H, d, J=9.0 Hz), 6.83 (2H, d, J=9.0 Hz), 6.94 (2H, d, J=9.0 Hz), 7.00 (2H, d, J=9.0 Hz).
IR (KBr) cm$^{-1}$: 3346,2960,1634,1611,1585,1571,1515, 1466, 1292,1252,1180,1035.
Mass (m/z): 394 (M$^+$).

Example 39

Preparation of 5,6-bis(4-Methoxyphenyl)-4-chloromethyl-2-isobutyl-2H-pyridazin-3-one Thionyl chloride (306.1 mg) was added to a solution of 5,6-bis(4-methoxyphenyl)-4-hydroxymethyl-2-isobutyl-2H-pyridazin-3-one (203 mg, 0.51 mmol) in benzene (10 ml), followed by stirring at 75° C. for 2 hours. Water was added to the reaction mixture, followed by extraction with chloroform. After the extract was dried over anhydrous sodium sulfate, the solvent was distilled off under reduced pressure. The residue was separated and purified by silica gel preparative chromatography [developer: hexane/ethyl acetate (2/1)], whereby the title compound (180.8 mg, 85.1%) was obtained as a yellow gum.
$^1$H-NMR (CDCl$_3$) δ: 1.03 (6H, dd, J=6.8, 1.0 Hz), 2.32–2.49 (1H, m), 3.73 (3H, d, J=1.5 Hz), 3.80 (3H, d, J=1.5 Hz), 4.12 (2H, d, J=7.3 Hz), 4.40 (2H, s), 6.71 (2H, dd, J=8.8, 1.0 Hz), 6.86 (2H, dd, J=8.8, 0.7 Hz), 7.02 (2H, dd, J=8.8, 0.7 Hz), 7.10 (2H, dd, J=8.8, 1.0 Hz).
IR (KBr) cm$^{-1}$: 1636,1615,1515,1466,1292,1252,1186, 1035, 1029.
Mass (m/z): 412 (M$^+$).

Example 40

Preparation of 5,6-bis(4-Methoxyphenyl)-2-cyclopropylmethyl-4-hydroxymethyl-2H-pyridazin-3-one Using 5,6-bis(4-methoxyphenyl)-4-carboxy-2-cyclopropylmethyl-2H-pyridazin-3-one as a starting material, the procedures of Example 38 were repeated likewise, whereby the title compound was obtained in a yield of 47.7%.
Colorless prisms (ethyl acetate-hexane)
Melting point: 124.5–124.9° C.
$^1$H-NMR (CDCl$_3$) δ: 0.46–0.53 (2H, m), 0.55–0.63 (2H, m), 1.47 (1H, ttt, J=8.1, 7.3, 4.9 Hz), 3.76 (3H, s), 3.81 (3H, s), 4.14 (2H, d, J=7.3 Hz), 4.40 (1H, t, J=6.6 Hz), 4.52 (2H, d, J=6.6 Hz), 6.71 (2H, d, J=8.9 Hz), 6.83 (2H, d, J=8.9 Hz), 6.94 (2H, d, J=8.9 Hz), 7.01 (2H, d, J=8.9 Hz).
IR (KBr) cm$^{-1}$: 1621,1582,1563,1513,1292,1251,1182, 1036, 835.
Mass (m/z): 392 (M$^+$).

Example 41

Preparation of 5,6-bis(4-Methoxyphenyl)-4-chloromethyl-2-cyclopropylmethyl-2H-pyridazin-3-one Using 5,6-bis(4-methoxyphenyl)-2-cyclopropylmethyl-4-hydroxymethyl-2H-pyridazin-3-one as a starting material, the procedures of Example 39 were repeated likewise, whereby the title compound was obtained quantitatively.
Colorless needles (chloroform-hexane)
Melting point: 117.8–118.6° C.
$^1$H-NMR (CDCl$_3$) δ: 0.48–0.54 (2H, m), 0.56–0.62 (2H, m), 1.49 (1H, ttt, J=7.8, 7.6, 4.9 Hz), 3.76 (3H, s), 3.83 (3H, s), 4.15 (2H, d, J=7.6 Hz), 4.41 (2H, s), 6.72 (2H, d, J=9.0 Hz), 6.87 (2H, d, J=9.0 Hz), 7.02 (2H, d, J=9.0 Hz), 7.10 (2H, d, J=9.0 Hz).
IR (KBr) cm$^{-1}$: 1649,1610,1514,1294,1255,1218,1179, 1027, 834.
Mass (m/z): 410 (M$^+$).

Example 42

Preparation of 5,6-bis(4-Methoxyphenyl)-2-sobutyl-4-phthalimidomethyl-2H-pyridazin-3-one Potassium phthalimide (324.4 mg) was added to a solution of 5,6-bis(4-methoxyphenyl)-4-chloromethyl-2-isobutyl-2H-pyridazin-3-one (180.8 mg, 0.44 mmol) in N,N-dimethylformamide (6 ml), followed by stirring at 80° C. for 2 hours. After the reaction mixture was concentrated, water was added, followed by extraction with ethyl acetate. The extract was dried over anhydrous sodium sulfate. The solvent was distilled off under reduced pressure. The residue was separated and purified by chromatography on a silica gel column and was then crystallized from ethyl acetate-hexane, whereby the title compound (215.8 mg, 94.1%) was obtained as colorless needles.

Melting point: 74.3–76.6° C.

$^1$H-NMR (CDCl$_3$) δ: 0.95 (6H, d, J=6.6 Hz), 2.28–2.40 (1H, m), 3.70 (3H, s), 3.74 (3H, s), 4.03 (2H, d, J=7.6 Hz), 4.80 (2H, s), 6.69 (2H, d, J=8.5 Hz), 6.71 (2H, d, J=8.5 Hz), 6.99 (2H, d, J=8.5 Hz), 7.04 (2H, d, J=8.5 Hz), 7.64 (2H, dd, J=5.4, 3.2 Hz), 7.72 (2H, dd, J=5.4, 3.2 Hz).

IR (KBr) cm$^{-1}$: 1717,1642,1611,1515,1467,1396,1290, 1250, 1179,1031,835,722,714.

Mass (m/z): 523 (M$^+$).

Test 1 Inhibitory Activity against Interleukin-1β Production

The following test was conducted, which showed inhibitory activity of the compounds of the present invention represented by the formula (1) against interleukin-1β production.

HL-60 cells were cultured for 4 days until confluence on RPMI 1640 medium with 10% fetal bovine serum (FBS) added thereto. The medium was centrifuged. The supernatant was discarded, and the cells were then suspended at 1×10$^6$ cells/ml on RPMI 1640 medium with 3% FBS, and lipopolysaccharide was added to give a final concentration of 10 μg/ml. The culture was inoculated at 1 ml/well to a 24-well plate. A test compound was added at 1 μl/well, followed by culturing for 3 days. Three days later, the amount of interleukin-1β in each culture was determined by ELISA. Each IC$_{50}$ value was determined by a comparison in yield with a control to which no test sample was added. Results on some representative compounds are shown in Table 1.

TABLE 1

Inhibitory Activity against Interleukin-1β Production

| Compound | Inhibitory activity against IL-β production (IC$_{50}$ μM) |
|---|---|
| Example 1 | 2.44 |
| Example 2 | 0.58 |
| Example 3 | 0.40 |
| Example 13 | 1.46 |
| Example 25 | 2.86 |
| Example 33 | 0.48 |
| Example 42 | 0.64 |
| Comp. Comp'd 1 | 29 |
| Comp. Comp'd 2 | 46 |
| Comp. Comp'd 3 | >100 |
| Comp. Comp'd 4 | 31.6 |

TABLE 1-continued

Inhibitory Activity against Interleukin-1β Production

| Compound | Inhibitory activity against IL-β production (IC$_{50}$ μM) |
|---|---|

(Comp. Comp'd 1)

(Comp. Comp'd 2)

(Comp. Comp'd 3)

(Comp. Comp'd 4)

As is apparent from Table 1, the compounds according to the present invention have been found to have extremely good inhibitory activity against interleukin-1β production compared with the comparative compounds, which are the compounds disclosed in Eur. J. Med. Chem., 14, 53–60, 1979.

Capability of Exploitation in Industry

The pyridazin-3-one derivatives (1) and their salts, which pertain to the present invention, have excellent inhibitory activity against interleukin-1β production, and are useful as medicines such as preventives and therapeutics for immune system diseases, inflammatory diseases and ischemic diseases.

What is claimed is:

1. A pyridazin-3-one compound represented by the following formula (1):

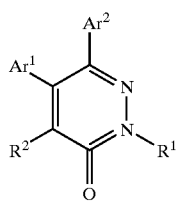

(1)

wherein $Ar^1$ represents a lower alkoxyphenyl group, $Ar^2$ represents a phenyl group having a lower alkoxy at least at the 4-position thereof, $R^1$ represents a linear or branched alkyl group having 2 to 11 carbon atoms, a cycloalkyl group having 3 to 7 carbon atoms, a lower alkyl group substituted by one or more cycloalkyl groups having 3 to 7 carbon atoms, or a phenyl or phenyl (lower alkyl) group which may be substituted by one or more of halogen atoms, lower alkyl groups and lower alkoxy groups, and $R^2$ represents a cyano group, a carboxyl group, a (lower alkoxy)carbonyl group, a substituted lower alkyl group or a substituted or unsubstituted carbamoyl group; or a salt thereof.

2. A pyridazin-3-one compound or a salt thereof according to claim 1, wherein $R^2$ is a cyano group; a carboxyl group; a lower alkoxycarbonyl; a lower alkyl group substituted by one or more of halogen atoms, hydroxy groups, and substituted or unsubstituted phthalimido groups; or a carbamoyl group which may be substituted by one or two of lower alkyl groups, aromatic groups and aromatic-group-substituted lower alkyl groups.

3. A pyridazin-3-one compound according to claim 1, which is 5,6-bis(4-methoxyphenyl)-4-carbamoyl-2-cyclopropylmethyl-2H-pyridazin-3-one, 5,6-bis(4-methoxyphenyl)-4-cyano-2-ethyl-2H-pyridazin-3-one, 5,6-bis(4-methoxyphenyl)-4-cyano-2-cyclopropylmethyl-2H-pyridazin-3-one, 5,6-bis(4-methoxyphenyl)-4-cyano-2-cyclopentylmethyl-2H-pyridazin-3-one, 2-benzyl-5,6-bis(4-methoxyphenyl)-4-ethoxycarbonyl-2H-pyridazin-3-one, 5,6-bis(4-methoxyphenyl)-4-ethoxycarbonyl-2-isopropyl-2H-pyridazin-3-one, or 5,6-bis(4-methoxyphenyl)-2-isobutyl-4-phthalimidomethyl-2H-pyridazin-3-one.

4. A pharmaceutical composition comprising a pyridazin-3-one compound or a salt thereof according to claim 1, and at least one pharmaceutically acceptable carrier or diluent.

5. A composition according to claim 4, wherein the pyridazin-3-one compound is present in an amount effective for inhibiting interleukin-1β production.

6. A composition according to claim 4, wherein the pryidazin-3-one compound is present in an amount effective for therapeutic treatment of a disease caused by stimulation of interleukin-1β production.

7. A composition according to claim 4, wherein the pyridazin-3-one compound is present in an amount effective for therapeutic treatment of an immune system disease, an inflammatory disease, an ischemic disease, osteoporosis or ichorrhemia.

8. A composition according to claim 4, wherein the pyridazin-3-one compound is present in an amount effective for therapeutic treatment of rheumatism, arthritis or inflammatory colitis.

9. A method for the treatment of a disease caused by stimulation of interleukin-1β production, which comprises
    administering a pyridazin-3-one compound or a salt thereof according to claim 1.

10. The method of claim 9, wherein the disease is selected from the group consisting of rheumatism, arthritis, osteoporosis, inflammatory colitis, immune system diseases, ichorrhemia, and ischemic disease.

11. A method for the treatment of a disease caused by stimulation of interleukin-1β production comprising
    administering a composition comprising the pyridazin-3-one compound of claim 1 to a mammal in need thereof.

12. The method of claim 11, wherein the pyridazin-3-one compound is administered in an amount of from 0.1 to 100 mg per day.

13. The method of claim 11, wherein the pyridazin-3-one compound is administered in an amount effective for inhibiting interleukin-1β production.

14. The method of claim 11, wherein the pyridazin-3-one compound is administered in one portion each day.

15. The method of claim 11, wherein the pyridazin-3-one composition is administered in a plurality of portions each day.

16. The method of claim 11, wherein the pyridazin-3-one composition is administered orally or parenterally.

17. The method of claim 11, wherein the mammal is in need of inhibitory activity against interleukin-1β production.

18. The method of claim 11, wherein the mammal is a human.

* * * * *